United States Patent [19] [11] Patent Number: 4,889,846
Crossley [45] Date of Patent: Dec. 26, 1989

[54] 3-(2,5-DISUBSTITUTED PHENYLAZO)-4-SUBSTITUTED PHENYLALKAN-1-OIC ACIDS AND ESTERS THEREOF AND METHOD OF TREATING INFLAMMATORY DISORDERS THEREWITH

[75] Inventor: Roger Crossley, Woodley, England

[73] Assignee: John Wyeth & Brother Limited, Maidenhead, England

[21] Appl. No.: 181,866

[22] Filed: Apr. 15, 1988

[30] Foreign Application Priority Data

Apr. 16, 1987 [GB] United Kingdom ............... 8709248

[51] Int. Cl.[4] .................. A61K 31/655; C07C 107/06; C09B 27/00; C09B 41/00
[52] U.S. Cl. .................................... 514/150; 534/578; 534/585; 534/587; 534/595; 534/599; 534/603; 534/728; 534/851; 534/852; 534/853
[58] Field of Search ................... 534/853, 852, 851; 514/150

[56] References Cited

U.S. PATENT DOCUMENTS 2,396,145  3/1946  Anders et al. ............... 534/853 X
4,628,083 12/1986  Agback ........................ 534/853 X
4,725,676  2/1988  Agback ........................ 534/853

FOREIGN PATENT DOCUMENTS 0021229  1/1981  European Pat. Off. ........... 534/853
1388920 11/1972  United Kingdom ............... 534/853

OTHER PUBLICATIONS

Klamann et al, Chemical Abstracts, vol. 55, 443$_{d-h}$ (1961).

Primary Examiner—Floyd D. Higel
Attorney, Agent, or Firm—George Tarnowski

[57] ABSTRACT

The invention concerns azo compounds of formula

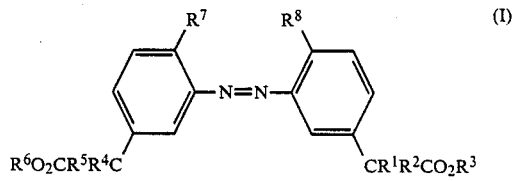

or a salt thereof, in which formula $R^1$, $R^2$, $R^3$, $R^4$, $R^5$, and $R^6$ are each independently hydrogen or lower alkyl, $R^7$ and $R^8$ are each independently alkyl of 1 to 7 carbon atom or cycloalkyl of 5 to 7 carbon atoms optionally substituted by lower alkyl which possess anti-inflammatory activity.

12 Claims, No Drawings

3-(2,5-DISUBSTITUTED PHENYLAZO)-4-SUBSTITUTED PHENYLALKAN-1-OIC ACIDS AND ESTERS THEREOF AND METHOD OF TREATING INFLAMMATORY DISORDERS THEREWITH

This invention relates to azo compounds more particularly to azodibenzene derivatives, to processes for preparing them and to pharmaceutical compositions comprising them.

This invention provides compounds of formula

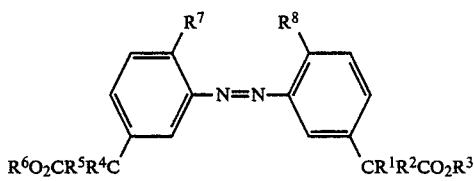

or salts thereof, in which formula $R^1$ to $R^6$ are independently hydrogen or lower alkyl, $R^7$ and $R^8$ are independently lower alkyl of 1 to 7 carbon atoms or cycloalkyl of 5 to 7 carbon atoms optionally substituted by lower alkyl.

Examples of each of $R^1$-$R^6$ are hydrogen, methyl, ethyl, n-propyl. Examples of each of $R^7$ and $R^8$ are isopropyl, isobutyl, sec.butyl, butyl, pentyl, cyclopentyl, cyclohexyl, cycloheptyl, 1-ethylcyclohexyl, 1-methylcyclohexyl.

Preferbly $R^3$ and/or $R^6$ are/is hydrogen. Preferably $R^7$ and/or $R^8$ are/is isobutyl. $R^1$ and $R^4$ are preferably hydrogen. Preferred values for $R^2$ and $R^5$ are independently methyl and ethyl. Most preferably the compounds of formula I are symmetrical, i.e. $R^7$ and $R^8$ are the same, as are $R^1$ and $R^4$, $R^2$ and $R^5$, and $R^3$ and $R^6$.

The compounds of formula I may possess one or more asymmetric centres and hence optical isomers are possible. All such isomers and mixtures thereof are within the scope of this invention.

In a particularly preferred aspect this invention provides a compound of formula

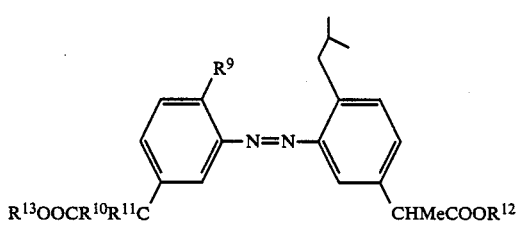

wherein $R^9$ is $C_3$-$C_7$ alkyl, preferably isobutyl; $R^{10-13}$ independently represent hydrogen or lower alkyl. Preferably $R^{10}$ is hydrogen and $R^{11}$ is methyl. Preferably $R^{12}$ is hydrogen.

The term 'lower' as used herein denotes 1 to 6 carbon atoms.

The compounds of formula I possess pharmaceutical activity in particular anti-inflammatory activity and hence are useful in the treatment of inflammatory diseases, such as rheumatoid arthritis and inflammatory bowel disease (including ulcerative colitis).

The compounds of formula I were tested for anti-inflammatory activity by the following general procedure: Groups of 6 male rats, weighing approximately 200 g were dosed orally twice daily for 2 days with either vehicle alone (hydroxypropylmethylcellulose/saline) or test drug in vehicle. After this pre-dosing period the rats were fasted overnight in separate cages and on the following day (i.e. Day 3) colonic damage was induced by administering 0.25 ml of a phenol/ethaol/water mixture (7.5:25:75) via a cannula introduced into the rectum and advanced into the colon. Dosing with the test drug continued for a further 24 hours after induction of colitis, after which time the rats were killed and the severity of colonic damage and/or inflammation assessed.

In the aforementioned test the representative compound 3,3'-azobis[α-methyl-4-(2-methylpropyl)benzeneacetic acid]dimethyl ester (compound A) gave the following results:

| Dose (po) | Description of appearance of colon |
|---|---|
| Compound A 100 mg/kg (in vehicle) | 1 rat had megacolon, with infected areas and ulceration<br>1 rat had moderate inflammation with ulceration<br>4 rats had slight inflammation with superficial mucosal damage |
| HPMC/saline (vehicle) | 1 rat had megacolon, with infected areas and marked inflammation<br>1 rat had marked inflammation with ulceration<br>2 rats had moderate inflammation with ulceration<br>2 rats had slight inflammation with ulceration |

These results show that compound A possesses good anti-inflammatory activity at the dose level tested.

This invention also provides processes for preparing the compounds of formula I. In general the compounds can be prepared by coupling procedures known to form an azo bond between appropriate starting material(s). Accordingly this invention provides a process for preparing a compound of formula I which comprises (a) coupling two molecules of a compound of formula

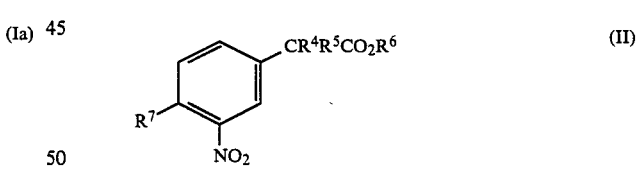

wherein $R^4$, $R^5$, $R^6$ and $R^7$ are as defined above using a reducing agent to give a corresponding symmetrical compound of formula I, or (b) coupling in the presence of copper or a copper salt (e.g. CuBr) two molecules of a diazonium salt of formula

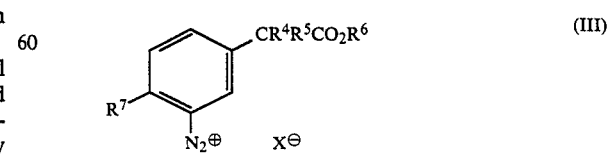

where $R^4$, $R^5$, $R^6$ and $R^7$ are as defined above and $X^\ominus$ represents an anion, e.g. chloride to give a symmetrical compound of formula I, or (c) coupling two molecules of a compound of formula:

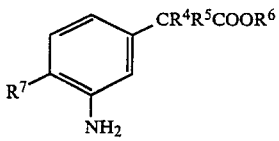

wherein $R^4$, $R^5$, $R^6$ and $R^7$ are as defined above using an oxidising agent, e.g. phenyliodosoacetate, lead tetraacetate, manganese dioxide, oxygen in the presence of base, e.g. KOBu$^t$ or sodium perborate to give a symmetrical compound of formula I, or (d) condensing a compound of formula

 (V)

with a compound of formula

 (VI)

in which formula one of Ar and Ar$^1$ represents the group

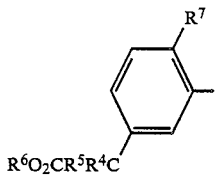

the other of Ar and Ar$^1$ represents the group

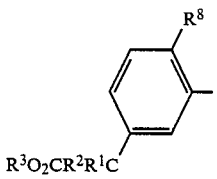

to give a corresponding compound of formula I or (e) esterifying a compound of formula I or a reactive derivative thereof wherein at least one of $R^3$ and $R^6$ is hydrogen to give a compound of formula I wherein $R^3$ and $R^6$ is lower alkyl, or (f) hydrolysing a compound of formula I wherein at least one of $R^3$ and $R^6$ is lower alkyl to give a compound of formula I wherein $R^3$ and $R^6$ are hydrogen, or (g) converting an acidic compound of formula I wherein at least one of $R^3$ and $R^6$ is hydrogen to a pharmaceutically acceptable alkali or alkaline earth metal or optionally substituted ammonium salt or acidifying such a salt to give an acidic compound of formula I.

With reference to process (a) the reductive coupling may be carried out using a deducing agent such as zinc in alkali, e.g. an alkali metal hydroxide, with heating if required. Strong reducing conditions should be avoided otherwise reduction to hydrazo compounds and other products may occur.

With reference to process (b) the diazonium salt may be prepared by reacting the hydrochloride salt of the corresponding amino compound with sodium or amyl nitrite at low temperature e.g. 0° C. in aqueous acid solution. Coupling of the diazonium salt may be effected in the presence of cuprous ion (CuCl) in aqueous solvents, e.g. acetone/water.

With reference to process (d) the reaction may conveniently be carried out under neutral or acidic conditions, e.g. in the presence of glacial acetic acid-see for example J. March, Advanced Organic Chemistry, Reactions, Mechanisms, and Structure, 2nd Edition, McGraw-Hill Book Co. and references cited therein p581.

With regard to esterification process (e) the acid maybe esterified in known manner, e.g. with a lower alkanol in acidic conditions, e.g. $H_2SO_4$ or Lewis acid such as $BF_3.Et_2O$. Alternatively the acid may be activated prior to reaction, e.g. by forming an acid halide.

The hydrolysis process (f) may be carried out in known manner e.g. by refluxing in aqueous alcoholic solvent under basic conditions, e.g. Na OH.

Acids of formula I may be converted to salts by reaction with suitable inorganic or organic bases. Suitable bases include, for example, the hydroxides, lower alkoxides, carbonates and bicarbonates of alkali metals, e.g. Na or K, alkaline earth metals, e.g. Ca, Mg as well as the bases, e.g. ammonia, triethylamine, benzylamine.

This invention also provides a pharmaceutical composition comprising a compound of formula I and a pharmaceutically acceptable carrier.

For the pharmaceutical compositions any suitable carrier known in the art can be used. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be encapsulating material. In powders the carrier is a finely divided solid which is in admixture with the finely divided active ingredients. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax and cocoa butter. The term "composition" is intended to include the formulation of an active ingredient with encapsulating material as carrier, to give a capsule in which the active ingredient (with or without other carriers) is surrounded by carriers, which is thus in associaion with it. Similarly cachets are included.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol containing from 10 to 75% of the glycol by weight is generally suitable. Other compositions can be made by dispersing the finely-divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 10 to 500 mg or more, e.g. 25 mg to 250 mg, according to the particular need and the activity of the active ingredient. The invention also includes the compounds in the absence of carrier where the compounds are in unit dosage form.

Based on the results from animal studies the dosage range for the treatment of humans using a compound of formula I will be in the range 10 to 1000 mg per day or more depending on the activity of the compound and the severity of the complaint.

In another aspect the invention provides as an anti-inflammatory agent a compound of formula I or a pharmaceutically acceptable salt thereof as defined above.

The following Examples illustrate the invention:

EXAMPLE 1

3,3′-Azobis[α-methyl-4-(2-methylpropyl)benzene acetic acid]

Damp, activated zinc (2 g, prepared by washing zinc powder [2.5 g] with 2N hydrochloric acid [100 ml] for 1 min, the mixture was filtered and the isolated metal was washed with water until the washings were neutral) was added portionwise to a mixture of 2-(4-(2-methylpropyl)-3-nitrophenyl)propionic acid (2 g), sodium hydroxide (1.6 g), water (3 ml) and ethanol (10 ml) at reflux. The mixture was heated at reflux a further 4½ hours.

The reaction mixture was filtered and the filtrates were acidified with 2N hydrochloric acid. The precipitate formed was isolated by filtration and was washed with water to give crude product (0.65 g).

This was recrystallised from di-isopropylether to give the title compound, quaterhydrate, mp. 208°–210° C.

Analysis. Found: C, 70.7; H, 8.0; N, 6.15%. $C_{26}H_{34}N_2O_4 \cdot \frac{1}{4}H_2O$ requires C 70.5; H, 7.85; N, 6.3%.

EXAMPLE 2

3,3′-Azobis[α-methyl(-4-(2-methylpropyl)benzeneacetic acid] dimethyl ester 3,3′-Azobis[α-methyl-4-(2-methylpropyl)benzeneacetic acid] (0.6 g) was added to a mixture of dichloromethane (15 ml) and thionyl chloride (1 ml) and stirred at room temperature for 3 hours. A further quantity of thionyl chloride (5 ml) was added and the mixtue was left to stir an additional 0.5 hours.

The solvent was removed under reduced pressure and the residue was heated at reflux in methanol.

The solvent was removed under reduced pressure and the residue was recrystallised from methanol to give the title compound. 0.3 g, mp. 87°–8° C.

Analysis. Found: C, 72.2; H, 8.2; N, 5.9%. $C_{28}H_{38}N_2O_4$ requires C 72.1; H, 8.2; N, 6.0%.

EXAMPLE 3

3,3′-Azobis[α-methyl-4-(2-methylpropyl)benzeneacetic acid] dimethyl ester.

The acid prepared in Example 1 (0.5 g) was suspended in methanol (20 ml) and 1 ml of $BF_3 \cdot Et_2O$ was added. The mixture was heated to reflux and the solids dissolved. After 1 hour the reaction mixture was evaporated under reduced pressure and the residue dissolved in ether washed ($Na_2CO_3$) and evaporated. The residue was recrystallised from methanol to give the title ester mp 88°–89°.

Analysis. Found: C, 72.0; H, 8.5; N, 5.9%. $C_{28}H_{38}N_2O_4$ requires C, 72.1; H, 8.2; N, 6.0%.

I claim:

1. A compound of formula I:

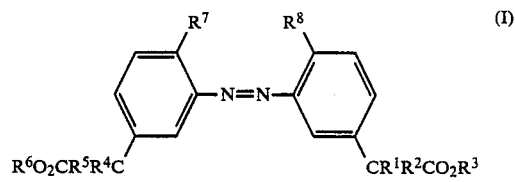

or a salt thereof, in which formula $R^1$, $R^2$, $R^3$, $R^4$, $R^5$, and $R^6$ are each independently hydrogen or lower alkyl, $R^7$ and $R^8$ are each independently alkyl of 1 to 7 carbon atom or cycloalkyl of 5 to 7 carbon atoms or cycloalkyl of 5 to 7 carbon atoms substituted by lower alkyl.

2. A compound as claimed in claim 1 wherein $R^1$, $R^2$, $R^3$, $R^4$, $R^5$, and $R^6$ are each selected from hydrogen, methyl, ethyl and n-propyl.

3. A compound as claimed in claim 1 wherein at least one of $R^7$ and $R^8$ is isobutyl.

4. A compound as claimed in claim 1 wherein $R^1$ and $R^4$ are both hydrogen.

5. A compound as claimed in claim 1 wherein $R^3$ and $R^6$ are both hydrogen.

6. A compound as claimed in claim 1 wherein $R^2$ and $R^5$ are each independently methyl or ethyl.

7. A compound of formula:

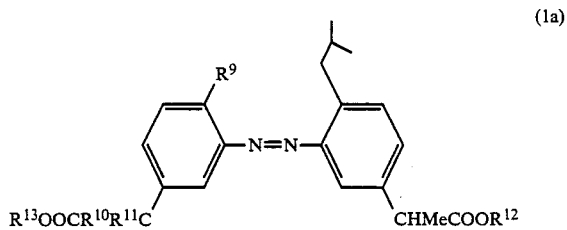

wherein $R^9$ is $C_3$–$C_7$ alkyl, $R^{10}$, $R^{11}$ and $R^{12}$ and $R^{13}$ are independently hydrogen or lower alkyl.

8. A compound as claimed in claim 1 which is 3,3′-azobis[α-methyl-4-(2-methylpropyl)benzeneacetic acid]dimethyl ester or a pharmaceutically acceptable salt thereof.

9. A compound as claimed in claim 1 which is 3,3′-azobis[α-methyl-4-(2-methylpropyl)benzeneacetic acid] or a pharmaceutically acceptable salt thereof.

10. A pharmaceutical composition comprising a compound of formula

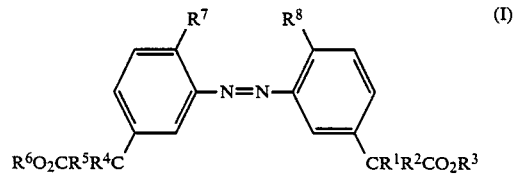

or a salt thereof, in which formula $R^1$, $R^2$, $R^3$, $R^4$, $R^5$, and $R^6$ are each independently hydrogen or lower alkyl, $R^7$ and $R^8$ are each independently alkyl of 1 to 7 carbon atom or cycloalkyl of 5 to 7 carbon atoms or cycloalkyl of 5 to 7 carbon atoms substituted by lower alkyl.

11. A method for the treatment of inflammatory disorders in a mammal so afflicted which comprises administering an effective amount of a compound of formula

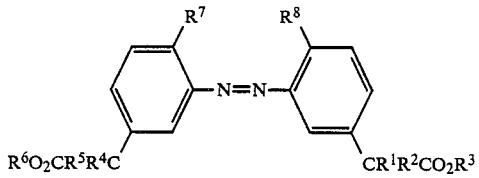

(I)

or a salt thereof, in which formula $R^1$, $R^2$, $R^3$, $R^4$, $R^5$, and $R^6$ are each independently hydrogen or lower alkyl, $R^7$ and $R^8$ are each independently alkyl of 1 to 7 carbon atom or cycloalkyl of 5 to 7 carbon atoms or cycloalkyl of 5 to 7 carbon atoms substituted by lower alkyl.

12. A method for the treatment of inflammatory bowel disease in a human so afflicted which comprises administering an effective amount of a compound of formula:

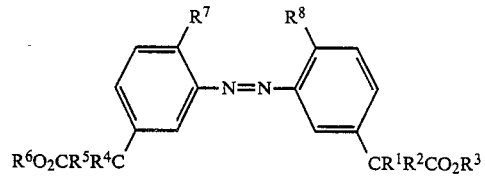

or a salt thereof, in which formula $R^1$, $R^2$, $R^3$, $R^4$, $R^5$, and $R^6$ are each independently hydrogen or lower alkyl, $R^7$ and $R^8$ are each independently alkyl of 1 to 7 carbon atom or cycloalkyl of 5 to 7 carbon atoms or cycloalkyl of 5 to 7 carbon atoms substituted by lower alkyl.

* * * * *